United States Patent [19]

Schaeffer et al.

[11] Patent Number: 6,015,683
[45] Date of Patent: Jan. 18, 2000

[54] DRY ANALYTICAL ELEMENT FOR ACETAMINOPHEN ASSAY

[75] Inventors: James Robert Schaeffer, Penfield; John Charles Mauck, Rochester; Robert Francis Winterkorn, Rochester; Thomas Charles Arter, Rochester, all of N.Y.

[73] Assignee: Clinical Diagnostic Systems, Inc., Rochester, N.Y.

[21] Appl. No.: 07/914,915

[22] Filed: Jul. 15, 1992

[51] Int. Cl.$^7$ .............................. C12Q 1/37; C12Q 1/26; C12Q 1/28; C12Q 1/00

[52] U.S. Cl. ................... 435/24; 435/4; 435/18; 435/25; 435/28; 435/966; 435/969; 435/970; 436/815

[58] Field of Search .................... 435/4, 18, 25, 435/28, 188, 189, 24, 966, 969, 970; 436/46, 93, 815; 422/55, 56, 57

[56] References Cited

U.S. PATENT DOCUMENTS

| | | | |
|---|---|---|---|
| 3,992,158 | 11/1976 | Przybylowicz et al. | 422/57 |
| 4,258,001 | 3/1981 | Pierce et al. | 422/56 |
| 4,292,272 | 9/1981 | Kitajima et al. | 422/57 |
| 4,357,363 | 11/1982 | Pierce et al. | 427/2 |
| 4,414,327 | 11/1983 | Hammond et al. | 435/18 |
| 4,424,150 | 1/1984 | Khanna | 530/300 |
| 4,430,433 | 2/1984 | Hammond et al. | 435/228 |
| 4,430,436 | 2/1984 | Koyama et al. | 436/531 |
| 4,504,413 | 3/1985 | Khanna | 435/188 |
| 4,605,754 | 8/1986 | Khanna | 560/19 |
| 4,675,290 | 6/1987 | Matsumoto et al. | 435/24 |
| 4,845,030 | 7/1989 | Batz et al. | 435/28 |
| 4,948,727 | 8/1990 | Cass et al. | 435/18 |
| 4,966,855 | 10/1990 | Deneke et al. | 435/28 |
| 4,999,288 | 3/1991 | deCastro et al. | 435/18 |
| 5,030,571 | 7/1991 | Best et al. | 435/227 |

FOREIGN PATENT DOCUMENTS

57/101760   6/1982   Japan.

*Primary Examiner*—Howard C. Lee

[57] ABSTRACT

A spectrophotometric assay for the detection of acetaminophen in aqueous fluids can be carried out with a dry analytical element. The element comprises a support having thereon one or more reagent layers containing a first enzyme, aryl acylamidase, to cleave the amide bond of acetaminophen to produce p-aminophenol; a second enzyme, ascorbic acid oxidase, to oxidize the p-aminophenol so that it couples to a water soluble coupling agent to form a dye that is read at 670 nm. The assay is precise, accurate on serum and plasma samples, and relatively free from significant interferences. The element also allows measurement over a broad dynamic range.

8 Claims, 3 Drawing Sheets

Acetaminophen Concentration mg/dL

A = 0.1   F = 3.9
B = 0.5   G = 5.2
C = 1.0   H = 9.8
D = 1.9   I = 20.2
E = 3.0   J = 29.4

Acetaminophen Concentration mg/dL

A = 0.1   F = 3.9
B = 0.5   G = 5.2
C = 1.0   H = 9.8
D = 1.9   I = 20.2
E = 3.0   J = 29.4

Acetaminophen Concentration mg/dL

A = 0.1  F = 3.9
B = 0.5  G = 5.2
C = 1.0  H = 9.8
D = 1.9  I = 20.2
E = 3.0  J = 29.4

DRY ANALYTICAL ELEMENT FOR ACETAMINOPHEN ASSAY

FIELD OF THE INVENTION

This invention relates to the field of clinical chemistry.

BACKGROUND OF THE INVENTION

Acetaminophen is a widely used analgesic. It is available without a prescription and is often used when aspirin may present problems to a patient. At therapeutic doses, serum concentration is usually below 50 mg/L. Toxicity is usually observed if the serum concentration four hours after ingestion of the drug is greater than 300 mg/L. One effect of overdose is liver toxicity. The need for an accurate method of determining the concentration of acetaminophen in serum is therefore apparent.

Known methods of assaying anilides such as acetaminophen utilize arylacylamidase (E.C.3.5.1.13) and an oxidizing agent. Arylacylamidase cleaves the amide bond of the anilide to produce acetate and an aniline such as p-aminophenol. The aniline is then made to react with with a color-forming compound like phenol in the presence of an oxidizing agent such as permanganate or the metal salts of copper or iron to form a color compound like indophenol which can be detected at 615 nm. Other methods use oxidizing agents like periodate, persulfates, or peroxidase. U.S. Pat. Nos. 4,999,288 and 4,430,433 are typical.

One disadvantage of these methods is that metal salts oxidize the aniline very slowly unless they are at alkaline pH, a condition that inactivates arylacylamidase.

U.S. Pat. No. 4,675,290 (issued Jun. 23, 1987, to Matsumoto) discloses a method of assaying peptidase enzyme activity which comprises treating a synthetic dibrominated amide (as substrate) with a sample containing peptidase thereby liberating a dibrominated aniline; oxidizing the thus-liberated dibrominated aniline with an oxidase (e.g. ascorbate oxidase) which consumes oxygen and forms pigment by oxidative condensation of said aniline in the presence of a coupler of a defined formula. This reaction takes place in solution.

Matsumoto's method uses an enzyme and might therefore overcome the problems encountered with the inorganic oxidizing agents of the prior art. However, Matsumoto employs a synthetic dibrominated substrate and is therefore not directly applicable to a test for acetaminophen. There is evidence in the art that in the case of oxidative coupling of phenols for color formation, color yield can be increased when certain halogenophenols are used in the color-forming reaction. However acetominophen as it appears in biological fluids to be tested is not halogenated and is therefore chemically distinguishable from the dibrominated synthetic substrate used in Matsumoto's method.

Further, Matsumoto disclosed a solution assay. An alternative and more convenient assay involves "dry" chemistry, a term that refers to methods and techniques that are carried out using chemical reagents contained in various "dry-to-the-touch" test elements such as "dip and read" test strips, multilayer test elements and the like. "Dry" methods require no liquid for reconstitution or analysis other than the test sample.

Reagents employed in solution assays often do not perform well when adapted to a dry format. Dry elements utilize minute amounts of reagents and test samples and so in a dry element for acetaminophen assay, it is important to employ reagents that give a clear and precise color signal when aniline is oxidatively coupled to a coupler to provide color.

The range of compounds that could be chosen as potential couplers is very wide. Matsumoto neither suggests nor gives guidance to those color forming oxidative couplers that would perform well in dry chemistry. The problem is that the selection of a suitable oxidative coupler for a dry element is essentially empirical.

It would be desirable to have a dry assay for determining acetominophen in biological fluids comprising enzymes and other reagents which remain active when combined and coated in dry format and which give a clear and precise signal on oxidative coupling with a suitable coupler.

SUMMARY OF THE INVENTION

The present invention selects for use a coupling agent that provides a detectable color change and precise determination of acetaminophen in a dry format. It was discovered that a water-soluble coupling agent was required and that a water-insoluble coupling agent, even if appropriately dispersed, did not work well.

The element of the present invention avoids the inorganic oxidizing agents taught by the prior art and uses instead a mild oxidizing agent, an enzyme. In dry analytical elements, oxidizing agents like $Cu^{++}$ and $Fe^{+++}$ are known to attack the gelatin matrix by crosslinking and thereby hardening the gelatin. The use of an enzyme overcomes this problem.

Accordingly, there is provided an analytical element for the determination of acetaminophen in an aqueous fluid comprising a support having thereon at least one reagent layer and containing in said reagent layer:

(A) an arylacylamidase enzyme;
(B) an oxidizing enzyme capable of oxidatively coupling paraaminophenol to a coupling agent to form a color compound; and
(C) a water-soluble, color-forming, coupling agent of the general structure:

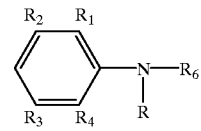

wherein R is $(CH_2)_n{}^-x$, where n=1–5 and x=$-(SO_3H)$,

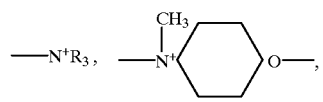

$(OCH_2CH_2)_yOH$ where y = 2-5.

$R_1$, $R_2$, $R_3$ and $R_4$ are independently hydrogen, alkyl, alkoxy, aryl, aryloxy, a heterocyclic group or halo, and $R_6$ represents hydrogen, straight or branched, substituted or unsubstituted alkyl 1 to 6 carbon atoms or $R_6$ is taken together with $R_1$ to represent the atoms necessary to complete a saturated 5 to 7 membered heterocyclic ring. $R_1$ may be the same as $R_2$, $R_3$ and $R_4$ or is taken together with $R_6$ as described above.

Another embodiment of the invention provides a method for determining acetaminophen in an aqueous liquid comprising the steps of:

A. contacting a sample of the aqueous liquid with the analytical element of claim 1 or 2; and
B. correlating the amount of color compound formed to the concentration of acetaminophen in the fluid.

An advantage of the invention is that the water soluble coupling agent and the enzyme-catalyzed oxidative coupling allow for a rapid reaction. We were able to develop a detectable color signal in 57 seconds. Water insoluble coupling agents involve much slower reactions.

It was surprising to find that in order to obtain an acceptable amount of color product in the desired time (5 minutes), it was necessary to combine a water soluble coupling agent and an enzyme. Even in solution assays, in order to obtain results in 5 minutes the oxidizing enzyme (e.g. ascorbate oxidase) had to be premixed with a water-soluble coupling agent prior to dilution with buffer. The reason for this is not known. While not wishing to be bound by scientific theories, Applicants believe that water solubility of the coupling agent allows it to mix sufficiently with the enzyme in the analytical element during storage (i.e. between manufacture and use). It appears that prior contact between the coupling agent and the oxidizing enzyme before reaction is necessary to obtain a satisfactory color reaction in 5 minutes.

DETAILED DESCRIPTION OF THE INVENTION

Figure 1:
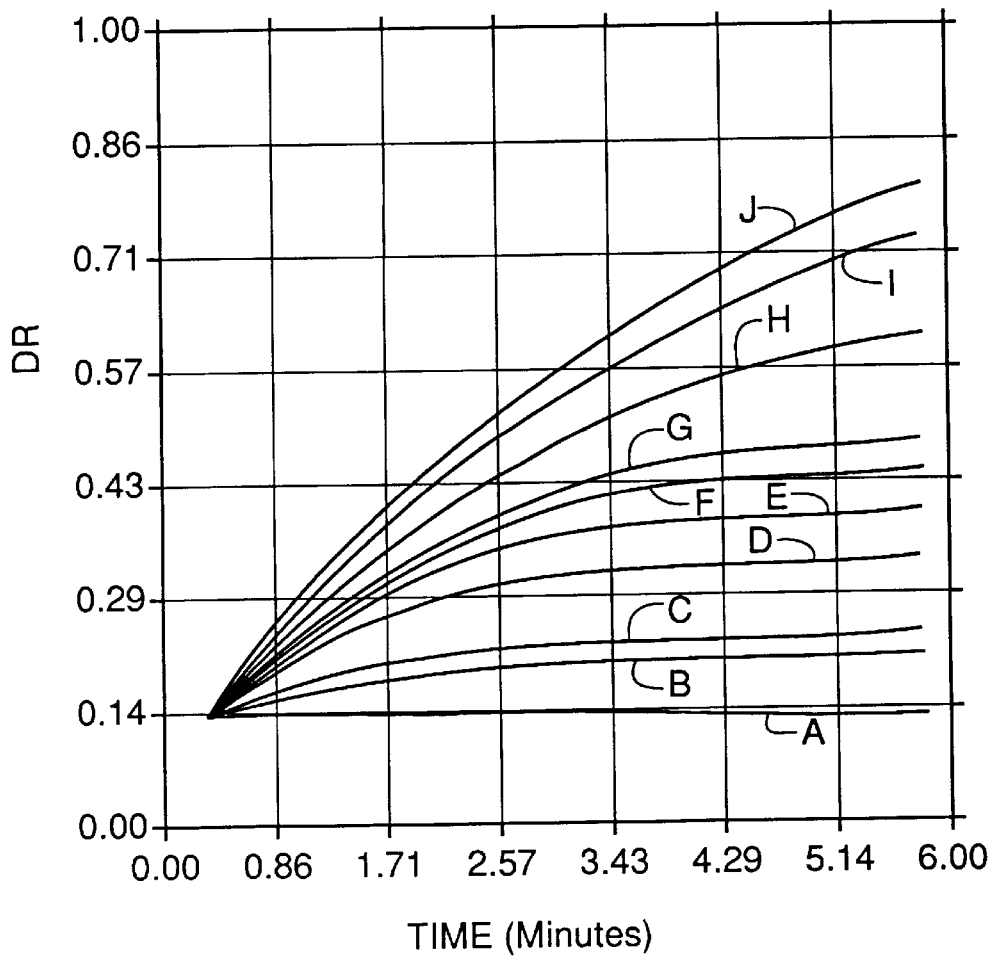
FIG. 1 is a graph showing the performance of an analytical element of the invention when 1-(3-sulfopropyl)-1,2,3,4-tetrahydroquinoline (compound #2, $THQSO_3H$) is used as the coupling agent.

The present invention discloses a colorimetric assay for the determination of acetaminophen based upon the enzymatic hydrolysis of acetaminophen and the subsequent detection of a metabolite of the hydrolysis. More specifically, the assay uses a first enzyme, aryl acylamidase (E.C.3.5.1.13), to cleave the amide bond of acetaminophen to produce acetate and p-aminophenol. A second enzyme such as ascorbic acid oxidase (E.C.1.10.3.3), tyrosinase (E.C.1.14.18.1), or laccase (E.C.1.10.3.2) oxidizes the p-aminophenol so that it couples to a water soluble coupling agent as defined herein, to form a dye. The dye is detectable at 670 nm. The reaction proceeds as follows:

examples is 1-(3-sulfopropyl)-1,2,3,4-tetrahydroquinoline, but it is believed that any species of the water soluble substituted aniline defined above would be useful. The screening procedures and their results are described below. The amount of color compound formed at the end of the reaction indicates the concentration of acetaminophen in the test sample.

The above-described reagents are coated on a support to provide a dry analytical element of the invention. Elements can be configured in a variety of forms, including elongated tapes of any desired width, sheets, slides or chips.

The elements can be used in manual or automated assay techniques. In general, in using the elements, acetaminophen determination is made by taking the element from a supply roll, chip packet or other source and physically contacting it with a sample (for example, up to 200 μL) of the liquid to be tested so that the sample and reagents interact sequentially within the element and become mixed. Such contact can be accomplished in any suitable manner, for example, by dipping or immersing the element into the sample or, preferably, by spotting the element by hand or machine with a drop of the sample with a suitable dispensing means.

After sample application, the element is incubated, for a period of up to 5 minutes, to facilitate color development. By incubation it is meant that the reagents are maintained at 37° C. in contact with each other for a period of up to 5 minutes before color measurements are made. Such fluids include, but are not limited to, whole blood, plasma, sera, lymph, bile, urine, spinal fluid, sputum, perspiration and the like as well as stool secretions. It is also possible to assay fluid preparations of human or animal tissue such as skeletal muscle, heart, kidney, lungs, brains, bone marrow, skin and the like.

Dry analytical elements useful for the assay of liquids can be prepared according to the teachings of U.S. Pat. No. 3,992,158 and U.S. Pat. No. 4,357,363 the contents of which are incorporated herein in their entirety.

Briefly described, the analytical element of this invention comprises one or more layers coated on a suitable support. All the reagents may be in a single layer coated on the support. Preferably, the reagents are coated in two distinct reagent layers as shown in Table I below. Whether contained in the same or in different layers of the element, all reagents must be in fluid contact with each other, meaning that reagents and reaction products can pass within a layer and between superposed regions of adjacent layers. In other words, when the element is contacted with an aqueous fluid, all reagents of the analytical composition of this invention are mixed sequentially as stated hereinbefore.

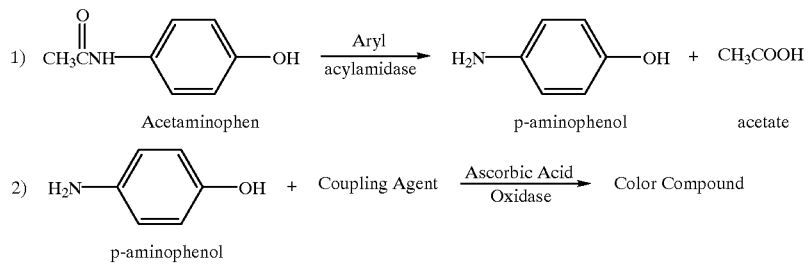

The water-soluble coupling agents useful in the present invention were identified by screening and selecting from among several potential couplers. The species in the The support can be any suitable dimensionally stable, and preferably, nonporous and transparent (i.e. radiation transmissive) material which transmits electromagnetic radiation of a wavelength between about 200 and about 900 nm. A radiation-transmissive support is particularly preferred to enhance and facilitate determination of detectable changes occurring in these elements by use of various radiation detection methods. A support of choice for a particular element should be compatible with the intended mode of detection (reflection, transmission or fluorescence spectroscopy). Useful support materials include polystyrene, polyesters [e.g. poly(ethylene terephthalate)], polycarbonates, cellulose esters (e.g. cellulose acetate), etc.

At least one reagent layer is coated on the support. The reagent layer(s) contain the indicator composition comprising one or more reagents dispersed in one or more synthetic or natural binder materials, such as gelatin or other naturally-occurring colloids, as well as different synthetic hydrophilic polymers such as poly(acrylamide), poly (vinylpyrrolidone), poly(acrylamide-co-N-vinyl-2-pyrrolidone), copolymers of the above, and polymers or copolymers to which crosslinkable monomers have been added.

The reagent layer may contain a buffer. Useful buffers include phosphate, pyrophosphate, tris(hydroxymethyl) aminomethane (TRIS), 2{[tris(hydroxymethyl)methyl) amino}-1-ethanesulfonic acid (TES), 4-(2-Hydroxyethyl)-1-piperazine-ethanesulfonic acid (HEPES), 3-[4-(2-Hydroxyethyl)-1-piperazinyl ]propanesulfonic acid (EPPES), 2-Hydroxy-3-{N-[tris(hydroxymethyl)methyl] amino}propanesulfonic acid (TAPSO), and other buffers with pH in the range of 6.5 to 8.5, preferably 7.5. The buffer may be in any or all layers of the element, or it may be in a separate layer devoid of other reagents.

Several surfactants such as Olin-10G™, TX™-102, TX-405™, Zonyl FSN™, but preferably TX-100™ and TX-165™ (a family of octylphenoxy polyethoxy ethanol nonionic surfactants sold by Rohm and Haas) may optionally be included in the reagent layer. Several different cross-linking agents are also optional, such as bisvinylsulfonylmethane, gluteraldehyde, etc.

The element may be provided with a porous, reflective spreading layer to uniformly distribute the liquid test sample over the element. The spreading layer may contain reagents, but preferably it is a distinct layer as shown in Table I below. Materials for use in spreading layers are well known in the art of making dry analytical elements as disclosed, for example, in U.S. Pat. No. 4,258,001 and the above cited patents.

Useful spreading layers can be prepared using fibrous materials, either mixed with a suitable binder material or woven into a fabric, as described in U.S. Pat. No. 4,292,272 (issued Sep. 29, 1981 to Kitajima et al), polymeric compositions or particulate materials, for example, a blush polymer such as disclosed in U.S. Pat. No. 3,992,158, beads bound together with or without binding adhesives, as described in U.S. Pat. No. 4,258,001 (issued Mar. 24, 1981 to Pierce et al), and U.S. Pat. No. 4,430,436 (issued Feb. 7, 1984 to Koyama et al) and Japanese Patent Publication 57(1982)-101760. Particularly useful spreading layers comprise barium sulfate or titanium dioxide. Since the sample is generally applied directly to the spreading layer, it is desirable that the spreading layer be isotropically porous, meaning that the porosity is the same in each direction in the layer as caused by interconnected spaces or pores between particles, fibers, or polymeric strands. An exemplary spreading layer is presented in Table I.

In one embodiment, the spreading layer contains N-ethyl maleimide, a compound found to be useful in blocking certain interferents which may be present in the test fluid. Commonly-owned U.S. application by T. C. Arter et al. titled *Sulfhydryl Complexing Agents in Clincal Test Elements* discloses this invention and is filed on even date herewith.

Other optional layers, e.g. subbing layers, radiation-blocking layers, etc. can be included if desired. The layers of the element can contain a variety of other desirable but optional components, including surfactants, thickeners, buffers, hardeners, bacteriostats, antioxidants, coupler solvents, and other materials known in the art. The amounts of these components are also within the skill of a worker in the art.

Changes in the element can be detected with suitable spectrophotometric apparatus, usually a reflectometer, using generally known procedures disclosed, for example, in U.S. Pat. No. 3,992,158 at Cols. 14–15 and U.S. Pat. No. 4,357,363 at Cols. 27. In an enzymatic reaction, the resulting product is determined by measuring, for example, the rate of change of reflection or transmission density in a finite area of the element of the invention contacted with the assay sample. The area measured is generally from about 3 to about 5 mm.

A representative element of this invention is presented in Table I below.

TABLE I

Acetaminophen Element

| | Coverage, g/m$^2$* | |
|---|---|---|
| | Useful Range | Actual Example |
| Reagents/Spreading Layer | | |
| Barium Sulfate | 75–120 | 100 |
| Cellulose | 1–20 | 8 |
| Surfactant TX-405TM | 0.2–4 | 1.6 |
| Estane | 1–15 | 12.3 |
| Maleimide | 0.1–3.0 | 1.0 |
| Subbing Layer | | |
| Polyvinylpyrrolidone | 0.5–2.5 | 1.0 |
| Reagent Layer 1 | | |
| Unhardened Gelatin | 4–24 | 6 |
| Surfactant TX-165 ™ | 0.005–0.1 | 0.01 |
| HEPES Buffer | 2–10 | 2.4 |
| Ascorbic Acid Oxidase | 50,000–300,000 IU/m$^2$ | 175,000 IU/m$^2$ |
| Arylacylamidase | 1,000–50,000 IU/m$^2$ | 5,000 IU/m$^2$ |
| Reagent Layer 2 | | |
| Hardened Gelatin | 4–24 | 6 |
| Coupler THQSO$_3$H | 0.2–2 | 1.0 |
| HEPES Buffer | 2–10 | 4.8 |
| Surfactant TX-165 ™ | 0.005–0.1 | 0.01 |

KEY
*g/m$^2$ except for ascorbic acid oxidase and arylacylamidase which are IU/m$^2$.
TX-405 ™:
TX-100 ™: a family of octylphenoxy and polyethoxy
TX-165 ™: ethanol sold by Rohm and Haas Co.
Triton X-100 ™:
THQSO$_3$H: Compound 2 of Table 1, i.e., 1-(3-Sulfopropyl)-1,2,3,4-tetrahydroquinoline
Estane: A polyester/polyurethane polymer sold by B. F. Goodrich.
HEPES: 4-(2-Hydroxyethyl)-1-piperazine-ethanesulfonic acid

TESTING FOR USEFUL COUPLING AGENTS

The following procedure was used to identify coupling agents which couple with p-aminophenol in the presence of ascorbic acid oxidase to give a strong color compound in solution. Such coupling agents were further tested for their performance in a dry analytical element for quantitatively assaying acetaminophen.

Three mL of a 0.1 M TRIS buffer at pH 7.5 was mixed with 300 μL of a solution containing 0.04 M of the coupling agent to be tested. To this solution was added 150 μL of ascorbic acid oxidase solution (4000 U/mL), 150 μL of arylacrylamidase solution (70 U/Ml), and 150 mL of an acetaminophen solution (300 mg/L). After 5 minutes absorbance was measured at 37° C. at a wavelength observed for the $\lambda_{max}$ for each dye. A spectrum of each dye solution was made between λ=300 and 800 nm in order to determine the $\lambda_{max}$ for each dye. Coupling agents which possessed an absorbance greater than 0.3 after 5 minutes were considered satisfactory for use in a dry analytical element (the 0.3 value was determined by subtracting the value of the coupling agent at the wavelength of the $\lambda_{max}$ of the dye). The absorbance values at 300 mg/L acetaminophen for a representative number of coupling agents are listed in Table II. The following nine compounds were among those tested as potential coupling agents:

TABLE II

Selection of Coupling Agents for Acetaminophen Assay

| Coupling Agent | λmax | Absorbance |
|---|---|---|
| 1. [structure: tetrahydroquinoline, N-C₄H₉] * | 670 nm | 0.36 (milky solution) |
| 2. [structure: tetrahydroquinoline, N-(CH₂)₃SO₃H] | 670 nm | 0.65 |
| 3. [structure: 8-hydroxy tetrahydroquinoline] * | 600 nm | 0.10 |
| 4. [structure: julolidine] * | 670 nm | 2.0 |
| 5. [structure: hydroxy-julolidine, OH] * | 500 nm | 0.23 |

TABLE II-continued

Selection of Coupling Agents for Acetaminophen Assay

| Coupling Agent | λmax | Absorbance |
|---|---|---|
| 6. [structure: N-ethyl-N-(2-sulfoethyl)-m-toluidine, NCH₂CH₂SO₃⁻Na⁺, CH₂CH₃, CH₃] | 650 nm | 0.12 |
| 7. [structure: 2-methylphenol (o-cresol), OH, CH₃] | 600 nm | 0.14 |
| 8. [structure: 3,5-dichloro-2-hydroxybenzoic acid, COOH, OH, Cl, Cl] | 550 nm | 0.06 |
| 9. [structure: 2,4,6-triiodobenzoic acid, COOH, I, I, I] | 650 nm | 0.04 |

*Compounds are water-insoluble. A DMF solution of the compound used was added to the analytical solution.

Figure 2:
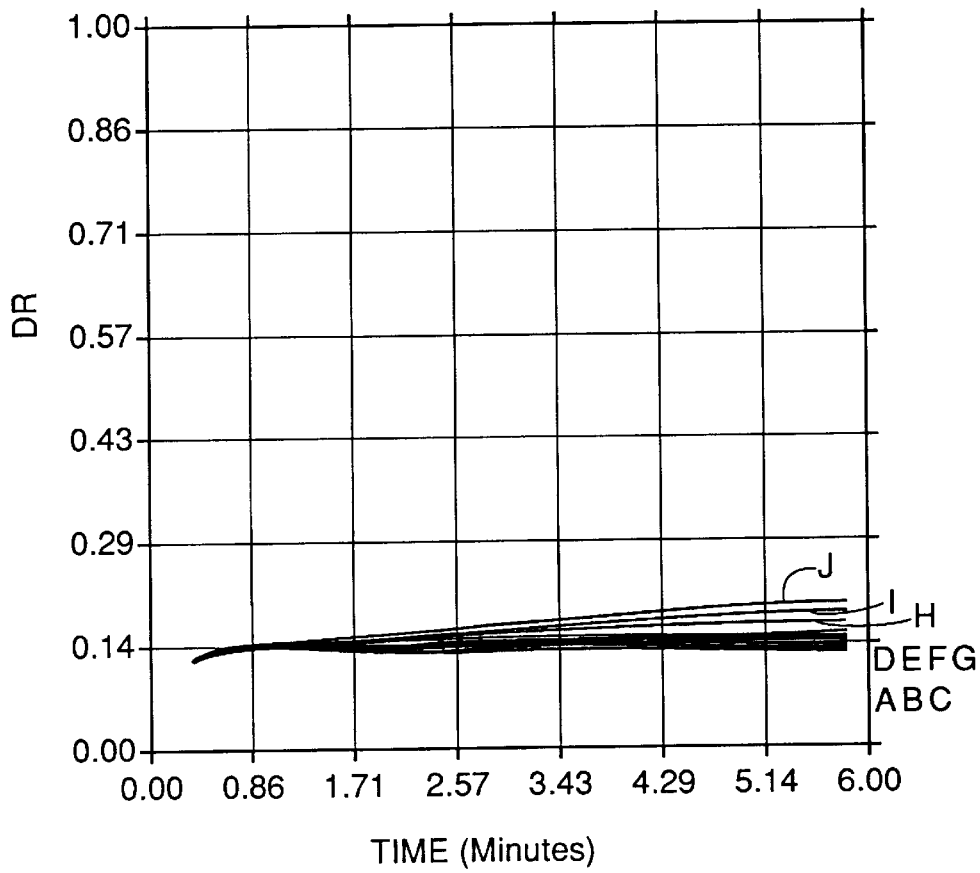
FIG. 2 is a graph showing the performance of a comparative element using 1-(n-butyl)1,2,3,4-tetrahydroquinoline (compound #1, BTHQ) as the coupling agent.
Figure 3:
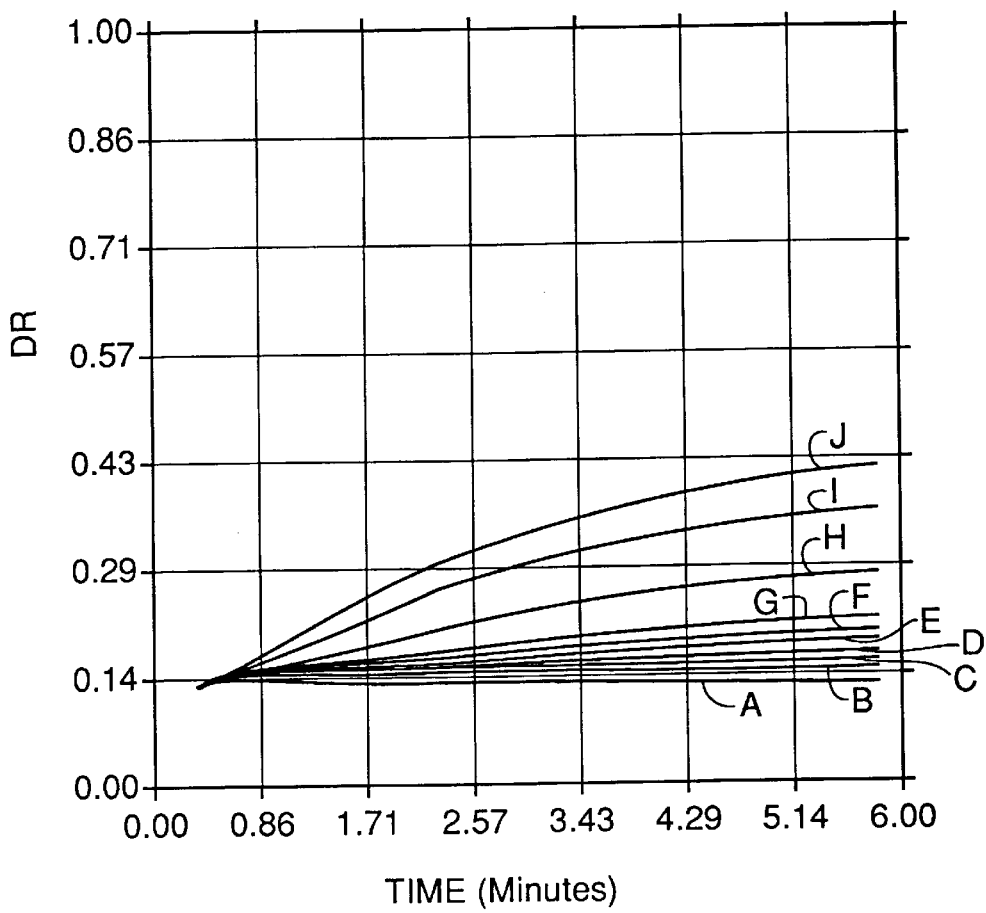
FIG. 3 is a graph showing the performance of another comparative element using benzo[ij]quinolizine, 1,2,3,5,6,7-hexahydro- (compound #4, Julolidine) as the coupling agent.

The data of Table II show that, of the coupling agents presented, only Compounds 1, 2 and 4 meet $D_T$ criteria and therefore were worth testing for use in a dry analytical element (i.e., λ=670, absorbance greater than 0.3), with compound 2 producing the highest sensitivity. Compounds 1 and 4 were not soluble without the addition of dimethyl formamide (DMF). When these compounds were dissolved in a KS-52 coupler solvent and then coated in a dry element of the invention (Examples 1, 2, and 3 below), they produced significantly less signal than compound #2. Results are shown in FIGS. 1, 2, and 3.

Preparation of 1-(3-sulfopropyl)-1,2,3,4-tetrahydroquinoline (compound #2, THO SO₃H)

A mixture of THQSO₃H (4.76 g, 40 mmole) and 1,3-propane sulfone (4.88 g, 40 mmole) in 50 ml reagent grade acetonitrile was heated under a nitrogen atmosphere and refluxed overnight. After cooling to room temperature, then to ice bath temperature, the resulting white solid was filtered and washed with cold acetonitrile. The yield was 8.1 g (84%), and the product had a melting point of greater than 200° C. Nuclear magnetic resonance (NMR) and elemental analysis showed the product to be consistent with the assigned structure. NMR (D₂O): 7.45 (s, 4H), 2.8–4.0 (m, 8H), 2.2 (t, 2H).

EXAMPLE 1

Coupling Agent Thoso$_3$H (NO. 2) in Analytical Elelment

After preparation, coupling compound #2 was coated in the element of the invention shown in Table 1 and tested for its performance in assaying varying known concentrations of acetaminophen in water (1.0, 5.4, 10.0, 19.0, 30.0, 39.0, 52.0, 98.0, 202.0, and 294.0 mg/L). Coating of the element can be carried out according to the teachings of U.S. Pat. Nos. 3,992,158, 4,357,363, and 4,258,001.

Kinetic response shown in FIG. 1 indicate that with this coupler good sensitivity is seen throughout the entire projected dynamic range ( 1 to 30 mg/dL).

COMPARATIVE EXAMPLE 2

Coupling Agent 1-(N-BUTYL) 1,2,3,4-TETRAHYDROQUINOLINE (COMPOUND #1, BTHO) IN ANALYTICAL ELEMENT Analytical elements were prepared and spotted with samples of varying concentrations of acetaminophen as in Example 1 except that coupling compound #1 (BTHQ) was used in place of compound #2 (THQSO$_3$H). Also, because compound NO. 1 is not water-soluble, it had to be dispersed in KS-52.

Results shown on FIG. 2 indicate that this coupling agent is not useful in the analytical element and provides a very narrow dynamic range.

Comparative Example Coupling Agent Benzo[ij] Quinolizine, 1,2,3,5,6,7-Hexahydro- (Compound #4, Julolidine)in Analytical Element Analytical elements were prepared and spotted with samples of varying concentrations of acetaminophen as in Example 1 except that coupling compound #4 (Julolidine) was used in place of compound #2 (THQSO$_3$H). Because compound NO. 4 is not water-soluble, it had to be dispersed in KS-52.

Results shown on FIG. 3 indicate that this coupling agent provides a very narrow dynamic range and so is not useful for our purposes.

Example 2

Tyrosinase as Oxidizing Agent in Element

This example was carried out as in Example 1 except that 6,400 U/m$^2$ of another oxidizing agent, tyrosinase, was used in place of 175,000 U/m$^2$ of ascorbic acid oxidase. Density response was measured using reflectance densitometry at 670 nm. Predictions were made by deriving a density/prediction spline for the densities produced and predicting the acetaminophen level of the sample from its density.

Predictions made based on the density response of the element (Table III) correlates well with the known acetaminophen concentration in the test fluids spotted on the element for testing.

Example Using Tyrosinase as Oxidizing Agent in Element

TABLE III

| Acetaminophen Level (mg/dL) | Density Response at 670 nm | Prediction (mg/dL) |
|---|---|---|
| 0.1 | .165 | 0.1 |
| 0.5 | .178 | 0.5 |
| 1.0 | .190 | 0.9 |
| 1.9 | .220 | 1.9 |
| 3.0 | .251 | 3.0 |
| 3.9 | .280 | 4.1 |
| 5.2 | .307 | 5.2 |
| 9.8 | .495 | 10.0 |
| 20.9 | .650 | 20.8 |
| 29.4 | .723 | 29.4 |

The invention has been described in detail with particular reference to a preferred embodiments thereof, but it will be understood that variations and modifications can be effected within the spirit and scope of the invention.

We claim:

1. An analytical element for the determination of acetaminophen in an aqueous fluid comprising a support having thereon at least one reagent layer and containing in said reagent layer:

(a) aryl acylamidase;

(b) an enzyme selected from the group consisting of ascorbic acid oxidase, tyrosinase and laccase; and (c) 1-(3-sulfopropyl)-1,2,3,4-tetrahydroquinoline.

2. A multilayer analytical element for the determination of acetaminophen in an aqueous fluid comprising a support having thereon, in order from said support and in fluid contact:

(a) one or more layers having therein aryl acylamidase; an enzyme selected from the group consisting of ascorbic acid oxidase, tyrosinase and laccase; and 1-(3-sulfopropyl)-1,2,3,4-tetrahydroquinoline; and (b) a porous spreading layer.

3. The analytical element of claim 1 or 2 further containing a buffer for maintaining the pH of the element in a range of about 6.5 to about 8.5.

4. The analytical element of claim 1 or 2 further containing maleimide in one or more of the layers.

5. A multilayer analytical element for the determination of acetaminophen in an aqueous fluid comprising a support having thereon, in order from said support, a first and second reagent layer wherein:

(a) the first reagent layer contains 1-(3-sulfopropyl)-1,2,3,4-tetrahydroquinoline;

(b) the second reagent layer contains ascorbic acid oxidase, aryl acylamidase; and (c) a porous spreading layer.

6. The analytical element of claim 5 further containing maleimide in one or more of the layers.

7. The analytical element of claim 6 wherein the maleimide is in the porous spreading layer.

8. A method for determining acetaminophen concentration in an aqueous liquid comprising the steps of:

(a) contacting a sample of the aqueous liquid with the analytical element of claim 1 or 2; and (b) correlating the degree of coloration to the concentration of acetaminophen in the fluid.

* * * * *